(12) United States Patent
Birrer et al.

(10) Patent No.: US 10,395,073 B2
(45) Date of Patent: Aug. 27, 2019

(54) METHOD FOR RFID TAG-READER ANTENNA ASSOCIATION IN A LABORATORY DEVICE

(71) Applicant: Roche Molecular Systems, Inc., Pleasanton, CA (US)

(72) Inventors: Armin Birrer, Udligenswil (CH); Riccardo Leone Benedetti, Fehraltorf (CH); Gregor Hotz, Zug (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 600 days.

(21) Appl. No.: 14/835,480

(22) Filed: Aug. 25, 2015

(65) Prior Publication Data
US 2016/0063287 A1 Mar. 3, 2016

(30) Foreign Application Priority Data
Aug. 28, 2014 (EP) ..................................... 14182590

(51) Int. Cl.
*G01N 35/00* (2006.01)
*G06K 7/10* (2006.01)
*B01L 3/00* (2006.01)

(52) U.S. Cl.
CPC ..... *G06K 7/10316* (2013.01); *G06K 7/10336* (2013.01); *G06K 7/10356* (2013.01); *B01L 3/545* (2013.01); *G01N 2035/00782* (2013.01); *G01N 2035/00801* (2013.01); *G01N 2035/00811* (2013.01)

(58) Field of Classification Search
CPC ............. G06K 7/0008; G06K 7/10009; G06K 7/10019; G06K 7/10316; G06K 7/10326; G06K 7/10336; G06K 7/10356

USPC ......................................................... 340/10.1
See application file for complete search history.

(56) References Cited

U.S. PATENT DOCUMENTS

| 8,035,485 B2 | 10/2011 | Fritchie | |
| 9,704,003 B1* | 7/2017 | Anderson | G06K 7/10366 |
| 2009/0002165 A1* | 1/2009 | Tuttle | G01S 3/48 |
| | | | 340/572.1 |

(Continued)

FOREIGN PATENT DOCUMENTS

EP 2690444 A1 1/2014

OTHER PUBLICATIONS

Catarinucci et al., Near Field UHF RFID Antenna System Enabling the Tracking of Small Laboratory Animals, Received Apr. 12, 2013; Revised May 31, 2013; Accepted Jun. 1, 2013, Hindawi Publishing Corporation, vol. 2013, Article ID 713943, 10 pages.*

*Primary Examiner* — Carlos Garcia
(74) *Attorney, Agent, or Firm* — Pamela C. Ancona; M. Reza Savari

(57) ABSTRACT

A method is provided for associating an RFID tag to an RFID reader antenna in a laboratory device with a number N RFID reader antennae, the method including the steps of reading a unique identifier corresponding to each of a number M of RFID tag(s); registering received signal strength indications by each of the N RFID reader antennae of corresponding response signals from each RFID tag(s) and associating each RFID tag with the reader antenna having received the strongest received signal strength indication corresponding to the RFID tag. A laboratory device is also provided which is configured to perform the disclosed method.

13 Claims, 2 Drawing Sheets

(56) References Cited

U.S. PATENT DOCUMENTS

| | | | |
|---|---|---|---|
| 2009/0278663 A1* | 11/2009 | Takeda | G06K 17/00 340/10.1 |
| 2010/0148985 A1 | 6/2010 | Lin et al. | |
| 2010/0237994 A1* | 9/2010 | Carraher | H04L 41/12 340/10.1 |
| 2011/0212859 A1 | 9/2011 | O'Banion et al. | |
| 2016/0033635 A1* | 2/2016 | Hansen | G01S 13/75 342/451 |
| 2017/0228688 A1* | 8/2017 | Bourlon | G06Q 10/087 |

* cited by examiner

METHOD FOR RFID TAG-READER ANTENNA ASSOCIATION IN A LABORATORY DEVICE

CROSS-REFERENCES TO RELATED APPLICATIONS

The present application claims the benefit of priority under 35 U.S.C. § 119 of EP 14182590.1, filed Aug. 28, 2014, the content of which is incorporated by reference herein in its entirety.

FIELD OF THE INVENTION

The present disclosure relates to the field of relates to a method for RFID tag-reader antenna association in a laboratory device, and further relates to a laboratory device configured to associate RFID tags with RFID reader antennae using the disclosed methods.

BACKGROUND OF THE INVENTION

In order to extend the reliability of tracking capabilities of resources such as consumables of laboratory devices, optically readable identifiers (such as barcodes or QR-codes) are being replaced or complemented by identifiers readable by the use of radio-frequency electromagnetic fields. Particularly common are radio frequency identification RFID tags enabling wireless, non-contact automatic identification and data capture.

While RFID tags provide major advantages over optically readable identifiers, such as no need for direct line of sight between identifier and reader, RFID technology also introduces certain disadvantages/difficulties. One such disadvantage is a consequence of the fact that an RFID reader antenna can communicate at the same time with all RFID tags within its range, and thus their individual identification/localization is not as straight-forward as for optically readable identifiers. In some scenarios such as inventory operations this aspect might not be problematic as only the presence/absence of an RFID tag is to be determined.

However, in many occasions it is very important that the correct identifier is addressed, such as when the exact location of an object or its relative location to an RFID reader antenna is to be identified. One particular field is the use of RFID tags to identify resources such as consumables of laboratory devices having multiple RFID reader antennae at loading/holding/processing positions (such as rack positions) of the resources. Since these loading/holding/processing positions of the resources are commonly located in relatively close proximity with respect to each other, addressing of an RFID of a neighboring position to the one where the particular RFID reader antenna is located is a common concern. One known approach to address this issue is for an RFID reader antenna to address all RFID tags in its vicinity and identify the RFID tag providing the strongest return signal as the tag located in the immediate proximity of the RFID reader antenna.

However, experience has shown that this approach often provides unsatisfactory results, i.e., in some occasions the wrong resource is identified to be present in a particular loading/holding/processing position. The consequences of two different consumables such as two different reagents being wrongly identified as being in a particular location in a laboratory device are extremely severe, such a mix-up having the potential to invalidate an entire batch of analysis, or even if the mix-up is not recognized, false results are reported by the laboratory device.

Embodiments of the disclosed method and device therefore aim to provide improved association of RFID tags to RFID reader antenna in a laboratory device, and in particular, to correctly identify resources of laboratory devices with their respective loading/holding/processing positions.

SUMMARY OF THE INVENTION

The main cause for unsatisfactory results of the aforementioned approach (i.e., addressing all RFID tags in the vicinity of an RFID reader antenna and identifying the RFID tag providing the strongest return signal as the tag located in the immediate proximity of the reader antenna) has been identified to be the variation of the strength of received signals from individual RFID tags. This variation of the strength of the received signal is a result of one or more of the following:

RFID tags and in particular RFID tag antennae of different types, e.g., from different manufacturers, from different batches/revisions/generations, materials and/or production tolerances;

Different ambient conditions in which the RFID tags operate, e.g., contact with a liquid, different ambient temperatures; different age of RFID tags potentially affecting their quality;

Physical surroundings of the loading/holding/processing positions of the laboratory device affecting the transmissibility of the radio frequency signals, such as the presence of metals;

Different batches/revisions/generations, materials and/or production tolerances of integrated circuits ICs of the RFID tags;

RFID tags with faulty/weak electrical contacts between their ICs and RFID reader antennae.

This variance in the strength of the received signal leads to inconsistent received signal strength indications RSSIs from multiple RFID tags. Thus the strength of the received signal is no longer a precise indicator for the position (e.g., distance) of the particular RFID tag relative to the reader antenna. For example the response signal from an RFID tag with a higher sensitivity might falsely indicate that it is located closer to the reader antenna than a second RFID tag of lower sensitivity which is actually the one in the immediate proximity of the reader antenna.

This problem is further amplified by the fact that the quality of the RFID tags attached to resources of laboratory devices is often out of the control of the manufacturer/user of a laboratory device, as resources (such as consumables) may be originating from different suppliers/vendors. Furthermore, unforeseen changes in the production of RFID tags during the long lifetime of laboratory devices must also be accommodated.

Therefore the disclosed subject matter is based on the recognition that the direct comparison of the absolute values of the received signal strength indications RSSIs from multiple RFID tags is not a reliable means to draw a conclusion(s) on the relative location of the RFID tags.

In order to provide accurate association between the location of an RFID tag and RFID reader antennae in a laboratory device, the presently disclosed subject matter could be conceptually summarized by the following major phases:

Sequential (to avoid reader collision) inventory by each RFID reader antennae of all RFID tags within their respective reach to obtain all unique identifiers thereof;

Registering received signal strength indications by each of the RFID reader antennae of from each RFID tags; and Associating each RFID tag with the RFID reader antenna which received the strongest signal from that particular RFID tag.

It shall be noted that between registering of the received signal strength and the association, the relative location of the RFID tags with respect to the RFID reader antennae should be unchanged. Alternatively—i.e., if the relative location of the RFID tags with respect to the RFID reader antennae does change—any correlation between respective locations of each RFID tag(s) with respect to the reader antennae must take such changes into account.

Accordingly, in one embodiment, the disclosed method for RFID tag-reader antenna association in a laboratory device including a number N RFID reader antennae includes the steps of:

reading a unique identifier corresponding to each of a number M of RFID tag(s);

registering received signal strength indications by each of the N RFID reader antennae of corresponding response signals from each RFID tag(s); and associating each RFID tag with the RFID reader antenna having received the strongest received signal strength indication corresponding to the RFID tag, wherein:

N and M are natural numbers,

N is greater than or equal to 2;

M is greater than or equal to 1.

Embodiments of the disclosed method/device are particularly advantageous as the method allows an accurate association of an RFID tag to the nearest RFID reader antenna irrespective of unpredictable inconsistencies in the sensitivity of individual RFID tags. The accurate association of an RFID tag to the nearest RFID reader antenna is achieved by means of always comparing response signals from the same RFID tags as received from different RFID reader antennae. Since the consistency of the sensitivity of the individual RFID reader antennae can be ensured to a very high degree and is in full control of the laboratory device manufacturer (as opposed to the sensitivity of the RFID tags), comparison of received signals of different RFID reader antennae coming from the same source (same RFID tag) can be fully relied on. Therefore embodiments of the disclosed method/device provide a great flexibility in the variance of the RFID tags attached to resources of the laboratory device to be located while ensuring high degree of accuracy in their association with an RFID reader antenna corresponding to a loading/holding/processing position in the laboratory device.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

DETAILED DESCRIPTION OF THE INVENTION

Figure 1:
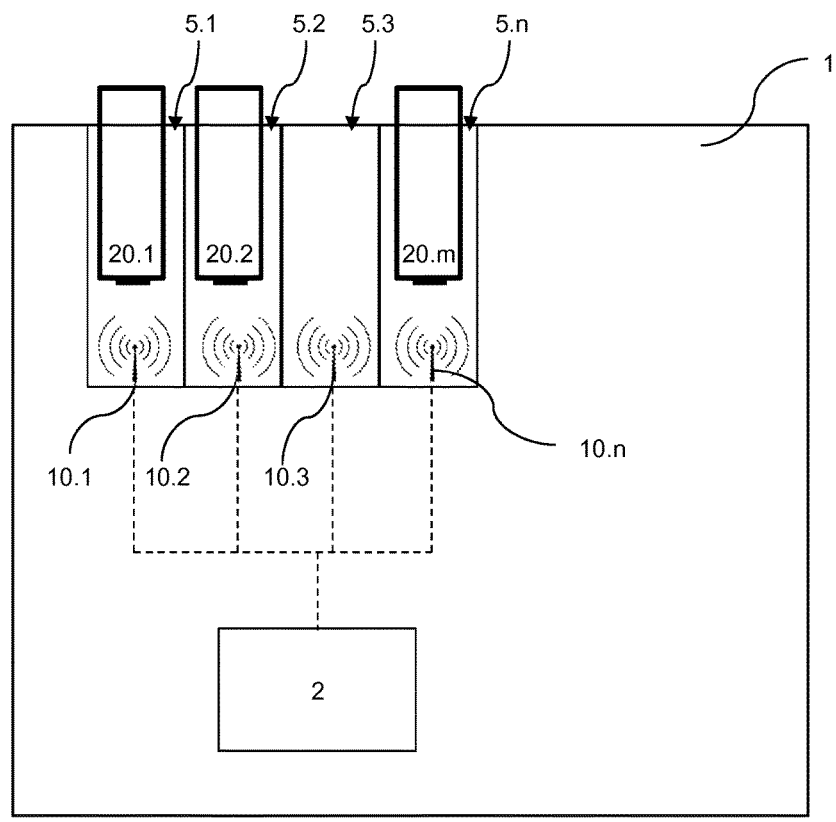
FIG. 1 shows a schematic block diagram of an embodiment of the disclosed laboratory.

By way of illustration, specific exemplary embodiments in which the disclosed subject matter may be practiced now are described.

Certain terms will be used in this patent application, the formulation of which should not be interpreted to be limited by the specific term chosen, but as to relate to the general concept behind the specific term.

The term "laboratory device" as used herein refers to any kind of automated; semi-automated or manual device for use in laboratory work in the clinical, chemical, biological, immunology or pharmaceutical area or the like. Such a laboratory device may comprise, amongst other things, at least one of an analytical instrument (such as clinical chemistry analyzers, coagulation chemistry analyzers, immunochemistry analyzers, urine analyzers), a transfer device (such as a conveyor, gripper, magnetic transfer surface), a storage unit, a liquid processing unit (such as a pipetting unit), a processor (such as a sample preparation device), a user interface, a mixing unit (such as a stirrer, a shaker or an agitator), a tempering device (such as a heater/cooler), a waste station, an aliquoter, a data management system, laboratory information system LIS or the like.

The term "RFID tag" as used in the context of the disclosed method refers to a passive RFID tag (in particular RFID tags operating in the HF range, i.e. below 100 MHz such as 13.56 MHz) that contains information. An RFID tag or transponder includes a coil or antenna and some information stored on an RFID chip that can be read and/or written by an RFID reader. Correspondingly the RFID tag can be read only or read/write and the information associated with the RFID tag can be hard-coded into the RFID tag at the time of manufacture or at some later time. The information stored on an RFID tag includes at least a unique identifier UID.

The term "RFID reader" as used herein includes devices that can read information from and/or write information into and/or lock information (i.e., prevent alteration of information on the RFID tag) on an RFID tag. RFID readers comprise or are connected to a reader antenna and circuitry to transmit and receive signals with the antenna. The RFID reader antenna generates an electromagnetic field, thereby transferring energy to the tag. Depending on the design of the RFID tag, a portion of the energy transferred to the tag will be absorbed by the tag, a modulation of the absorption providing information about the tag back to the reader.

The term "individually addressing"—with respect to an RFID reader individually addressing an RFID tag—as used herein shall refer to any mode of addressing an RFID tag by means of which only the individually addressed RFID tag responds. The modes of individually addressing an RFID tag comprise but are not limited to the "addressed mode" and the "selected mode", both using the UID of the RFID tag to individually address it.

The term "vicinity" as used herein with respect to an RFID tag being in the vicinity of an RFID reader antenna shall mean a distance of up to about 1-1.5 meters (as defined by the ISO 15693 standard).

The term "proximity" as used herein with respect to an RFID tag being in the proximity of an RFID reader antenna shall mean a distance of up to about 10 cm (as defined by the ISO 14443 standard).

The term "association"—with respect to an RFID tag and an RFID reader antenna—as used herein refers to defining a relationship between the RFID tag and the antenna of the reader reflecting their relative position with respect to each other. In one embodiment the RFID tag-reader antenna associations are represented in the form of a look-up table stored in a computer memory, the table including a table cell corresponding to each RFID tag and having as table cell value the identifier of the particular antenna which is determined to be closest to that RFID tag. It will be understood that many variations of how this association can be represented could be adopted without departing from the scope of the disclosed method/device.

The term "resource" as used herein refers to reagent(s)/reagent cassette(s) or consumable(s) of a laboratory device. The term "reagent" is used to indicate a composition required for treatment of a sample. Reagents may be any liquid, e.g., a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g., to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, etc. A "reagent cassette" can refer to a container including a liquid or suspension of reagents. Or a reagent cassette can be a holder for holding containers including a liquid or a suspension of reagents.

A "consumable" is understood to be a device which is introduced recurrently to the laboratory device for use in an analytical test. A consumable may be used a single time before being replaced, or it may be use multiple times. Examples of consumables include pipette tips, tip racks, vessels, reagent containers etc.

According to embodiments of the disclosed method/device, the RFID tag(s) 20.1-20.M are attached to and/or associated with corresponding resources of the laboratory device 1 including one or more of the following (non-exhaustive list):

consumable(s) and/or consumable carrier(s);
sample(s) and/or sample carrier(s);
tip(s) and/or tip carrier(s);
strip(s) and/or strip carrier(s);
reagent(s) and/or reagent carrier(s).

The terms "loading/holding/processing position(s)" as used herein shall refer to:

loading position(s): physical or functional location(s) of a laboratory device configured for loading/receiving a resource, such as an input tray or rack;
holding position(s): physical or functional location(s) of a laboratory device configured for holding/storing a resource, such as a storage rack for reagents, a cooling unit or the like;
processing position(s): physical or functional location(s) of a laboratory device configured for enabling processing (such as pipetting) a resource.

According to certain embodiments, the loading and/or holding and/or processing position(s) can coincide, i.e. resources may be loaded and/or held and/or processed at the same physical or functional location(s) of a laboratory device.

FIG. 1 shows a laboratory device 1 according to one embodiment of the disclosed method/device, the laboratory device 1 having a number N RFID reader antennae 10.1-10.N associated with N holding positions 5.1-5.N for resources. The RFID reader antennae 10.1-10.N are RFID antennae of the known kind arranged and configured to read information from a number M RFID tags 20.1-20.M loaded into respective holding positions 5.1-5.N.

As the number N of antennae 10.1-10.N correspond to loading/holding/processing positions 5.1-5.N for receiving resources to which the number M RFID tags 20.1-20.M are attached to, it shall be noted that:

N and M are natural numbers (1, 2, 3 . . . );
N is greater than or equal to 2
(as there is no need for determining a location when there is only one antenna i.e. only one holding position);
M is greater than or equal to 1.

In a first step of the method, the unique identifier $UID_1$-$UID_M$ corresponding to each of a number M of RFID tag(s) 20.1-20.M is read in order to obtain a list/inventory of the UIDs of all RFID tags loaded in the laboratory device 1.

In certain embodiments—as shows on FIG. 1 for example, the RFID reader antennae 10.1-10.N are each configured to read a unique identifier $UID_1$-$UID_M$ corresponding to each of a number M RFID tag(s) 20.1-20.M at loading and/or holding and/or processing position 5.1-5.N.

Furthermore, the N RFID reader antennae 10.1-10.N are each configured to register the received signal strength indication(s) RSSI.1.1-RSSI.N.M of the corresponding response signals from RFID tag(s) 20.1-20.N based on which the RFID tag-reader antenna association shall be made.

According to certain embodiments, the received signal strength indications RSSI.1.1-RSSI.N.M are registered by each of the N RFID reader antennae 10.1-10.N in the same step/while reading the unique identifier $UID_1$-$UID_M$ corresponding to each of the M RFID tag(s) 20.1-20.M. In other words, the received signal strength indications RSSI.1.1-RSSI.N.M are registered from the same response as the one carrying the unique identifier $UID_1$-$UID_M$.

According to further embodiments, the received signal strength indications RSSI.1.1-RSSI.N.M are registered by each of the N RFID reader antennae 10.1-10.N in a separate step, in particular by individually addressing each of the M RFID tag(s) 20.1-20.M by means of the corresponding unique identifier(s) $UID_1$-$UID_M$.

In alternative embodiments—not shown on the figures—the unique identifiers $UID_1$-$UID_M$ are read by means of RFID readers positioned at a different location of the laboratory device 1 where each resource to be identified will first pass by (e.g., at an opening door or drawer for the resources such as a reagent cassette loading drawer).

In alternative embodiments—not shown on the figures—the unique identifiers $UID_1$-$UID_M$ corresponding to each of a number M of RFID tag(s) 20.1-20.M are read out of a computer memory comprised by or communicatively connected to the laboratory device 1. As shown on FIG. 1, the laboratory device 1 further comprises a processing unit 2 configured to associate each RFID tag 20.1-20.M with the reader antenna 10.1-10.N having received the strongest received signal strength indication RSSI.1.1-RSSI.N.M corresponding to the RFID tag 20.1-20.M.

In some embodiments, this association is based on a table in which the received signal strength indication(s) RSSI.1.1-RSSI.N.M of the corresponding response signals from RFID tag(s) 20.1-20.N are registered to, table which in one embodiment resembles table 1 below:

TABLE 1

RSSI: Values by RFID Tag and Antenna

| RFID tag | $UID_1$-$UID_M$ | RSSI at | RSSI at | RSSI at | RSSI at | RSSI at |
|---|---|---|---|---|---|---|
| 20.1 | E0XX0100FFFF19 | 157 | 149 | 0 | 0 | 0 |
| 20.2 | E0XX000012341B | 118 | 125 | 119 | 0 | 0 |
| 20.3 | E0XX0100FFFF1D | 0 | 117 | 135 | 122 | 0 |
| 20.4 | E0XX0100FFFF19 | 0 | 0 | 124 | 158 | 126 |
| 20.5 | E0XX0100FFFF19 | 0 | 0 | 0 | 123 | 157 |

Table 1 illustrates very well how the hereby disclosed method overcomes the problems arising from RFID tags of different sensitivity. For example as in the table above, the second reader antenna 10.2 records a higher RSSI value for the first RFID tag 20.1 (a relatively strong tag) than for the second RFID tag 20.2 (a relatively weak tag). In this case the prior known methods would erroneously conclude that the first RFID tag 20.1 is located closest to the second reader antenna 10.2. However this is not correct and the error using known methods would be due to the lower sensitivity of the second RFID tag 20.2 which despite being the one closest to the second antenna 10.2, it transmits a response with a slightly weaker RSSI value than the first RFID tag 20.1 which is further away.

As opposed thereto, using the method of the disclosed method/device, by comparing the RSSI values for the second RFID tag 20.2 as received by multiple RFID reader antennae, the processing unit 2 correctly associates the second RFID tag 20.2 as being closest to the second reader antenna 10.2.

In one embodiment, as a further step to reduce errors, the method further comprises the step of verifying that no more than one RFID tag 20.1-20.M is associated with each reader antenna 10.1-10.N.

In addition to associating each RFID tag 20.1-20.M with the reader antenna 10.1-10.N having received the strongest received signal strength indication RSSI.1.1-RSSI.N.M corresponding to the RFID tag 20.1-20.M, certain embodiments further comprise the step of providing a correlation between the respective locations of each of the M RFID tag(s) 20.1-20.M and the loading and/or holding and/or processing positions 5.1-5.N based on the association between the RFID tag(s) 20.1-20.M with the RFID reader antennae 10.1-10.N. It shall be noted that the steps of providing the association and correlation may be performed at the same time even as a single operation/step.

In order to ensure that the correct RFID tag 20.1-20.M is communicated with, after the association has been provided, communication(s) between the laboratory device 1 and a particular RFID tag 20.1-20.M is directed through the reader antenna 10.1-10.N associated with the particular RFID tag 20.1-20.M, each reader antenna 10.1-10.N communicating by individually addressing the associated RFID tag 20.1-20.M, i.e. by means of the so-called RFID addressed mode commands.

According to further embodiments of the disclosed method/device, an error signal is generated if based on reading the unique identifiers $UID_1$-$UID_M$ corresponding to each of the M of RFID tag(s) 20.1-20.M, the number M of RFID tag(s) 20.1-20.M is greater than the number N of RFID reader antennae 10.1-10.N. This could be due to an RFID tag label which fell of a resource being "stuck" in the laboratory device, or a resource accidentally having more than one RFID tag attached.

In further embodiments of the disclosed method/device, an error signal is generated if based on reading the unique identifiers $UID_1$-$UID_M$ corresponding to each of the M of RFID tag(s) 20.1-20.M, the number M of RFID tag(s) 20.1-20.M is different than a number R of resources detected as being present in loading and/or holding and/or processing position(s) of the laboratory device 1. As one resource is to be associated with/identified by one RFID tag 20.1-20.M, the presence of more resources than RFID tags is an indication that at least one resource cannot be identified. This could be the case when a resource lacks an RFID tag, has a defect RFID tag attached or when the resource is erroneously loaded such that the RFID tag is not within the range of the RFID reader antenna. The number R of detected resources may be determined by means independent from the RFID tags of the resources such as by optical detection; by weight measurement; by electro-mechanical contacts (switches), etc.

Figure 2:
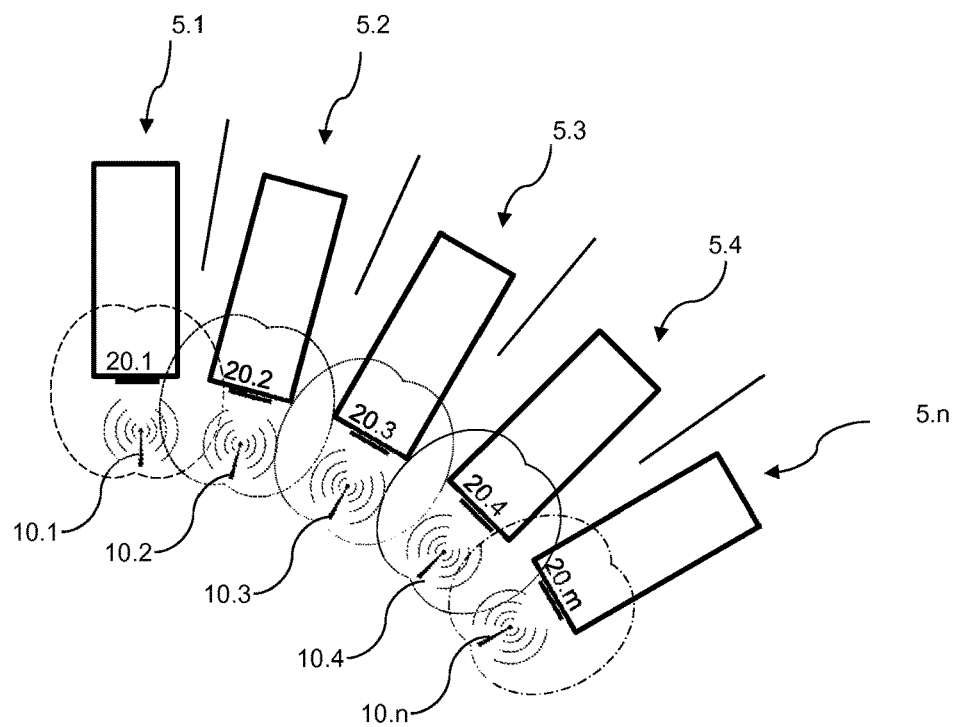
FIG. 2 shows a top view of multiple RFID tags attached to reagent cassettes for a laboratory device arranged along an arc of a carrousel-like cassette holder with an RFID reader antenna for each position of the carrousel.

FIG. 2 shows a top view of multiple RFID tags 20.1-20.M attached to resources (such as consumables, e.g. reagent cassettes) for a laboratory device 1 arranged along an arc with an RFID reader antenna 10.1-10.N for each holding position 5.1-5.N. In the embodiment depicted herein, the holding positions 5.1-5.N are positions of a carrousel-like cassette holder for reagent cassettes or the like). As illustrated on this figure with variously dashed lines, the reading range of one reader antenna 10.1-10.N is large enough so that more than one RFID tag 20.1-20.M may be located therein.

Figure 3:
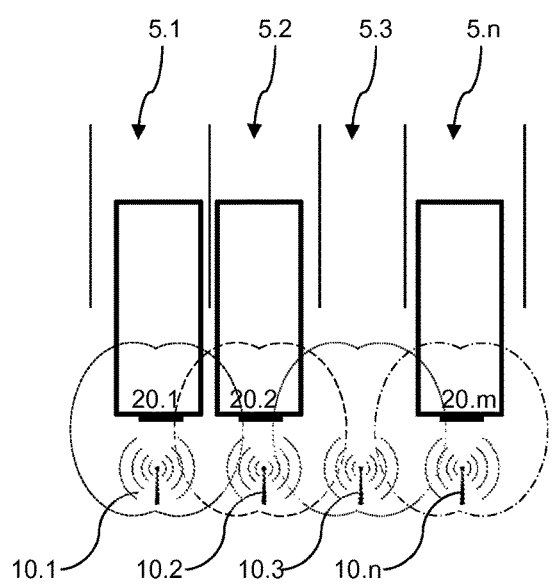
FIG. 3 shows a top view of multiple RFID tags attached to reagent cassettes for a laboratory device arranged linearly corresponding to a rack-like cassette holder with an RFID reader antenna for each position of the rack.

FIG. 3 shows a top view of a further embodiment wherein multiple RFID tags 20.1-20.M attached to reagent cassettes for a laboratory device 1 are arranged linearly corresponding to a rack-like cassette holder with an RFID reader antenna 10.1-10.N for each holding position 5.1-5.N of the rack.

While the foregoing embodiments have been described in some detail for purposes of clarity and understanding, it will be clear to one skilled in the art from a reading of this disclosure that various changes in form and detail can be made without departing from the true scope of the subject matter. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for radio frequency identification RFID tag-reader antenna association in a laboratory device comprising a number N RFID reader antennae, the method comprising the steps:
   reading a unique identifier corresponding to each of a number M of RFID tag(s);
   registering received signal strength indications by each of the N RFID reader antennae of corresponding response signals from each of the M RFID tag(s); and
   associating each of the M RFID tag(s) with the reader antenna having received the strongest received signal strength indication corresponding to the RFID tag, and generating an error signal if, based on reading the unique identifiers corresponding to each of the M of RFID tag(s), the number M of RFID tag(s) is (i) greater than the number N of RFID reader antennae, or (ii) different than a number R of resource(s) detected as being present in loading and/or holding and/or processing position(s) of the laboratory device, wherein:

R, N and M are natural numbers;

N is greater than or equal to 2; and

M is greater than or equal to 1.

2. The method according to claim 1, wherein the received signal strength indications are registered by each of the N RFID reader antennae while reading the unique identifier corresponding to each of the M RFID tag(s).

3. The method according to claim 1, wherein the received signal strength indications are registered by each of the N RFID reader antennae by individually addressing each of the M RFID tag(s) by means of the corresponding unique identifier(s).

4. The method according claim 1, wherein each reader antenna is located at a loading and/or holding and/or processing position of resource(s) of the laboratory device, the method further comprising the step of providing a correlation between respective locations of each of the M RFID tag(s) and the loading and/or holding and/or processing positions based on the association between the RFID tag(s) with the RFID reader antennae.

5. The method according to claim 1, further comprising the step of:

directing communication(s) between the laboratory device and a particular RFID tag through the reader antenna associated with the particular RFID tag, each reader antenna communicating by individually addressing the associated RFID tag.

6. The method according to claim 1, wherein the RFID tag(s) are attached to and/or associated with corresponding resources of the laboratory device comprising one or more of the following:

consumable(s) and/or consumable carrier(s);

sample(s) and/or sample carrier(s);

tip(s) and/or tip carrier(s);

strip(s) and/or strip carrier(s);

reagent(s) and/or reagent carrier(s).

7. The method according to claim 1, further comprising the step of verifying that no more than one RFID tag is associated with each reader antenna.

8. A laboratory device comprising a number N RFID reader antennae:

configured to read a unique identifier corresponding to each of a number M RFID tag(s);

each configured to register received signal strength indications of corresponding response signals from RFID tag(s);

a processing unit configured to (i) associate each of the M RFID tag(s) with the reader antenna having received the strongest received signal strength indication corresponding to the RFID tag, and (ii) generate an error signal if, based on reading the unique identifiers corresponding to each of the M of RFID tag(s), the number M of RFID tag(s) is (i) greater than the number N of RFID reader antennae, or (ii) different than a number R of resource(s) detected as being present in loading and/or holding and/or processing position(s) of the laboratory device, wherein:

N and M are natural numbers;

N is greater than or equal to 2; and

M is greater than or equal to 1.

9. The laboratory device according to claim 8, wherein the N RFID reader antennae are configured to register the received signal strength indications while reading the unique identifier corresponding to each of a number M RFID tag(s).

10. The laboratory device according to claim 8, wherein the N RFID reader antennae are configured to register the received signal strength indications by individually addressing each of the M RFID tag(s) by means of the corresponding unique identifier(s).

11. The laboratory device according to claim 8, further comprising loading and/or holding and/or processing positions for resources of the laboratory device, wherein the RFID tag(s) are attached to and/or associated with corresponding resources and wherein one of the N RFID reader antennae is located at and/or associated with a loading and/or holding and/or processing position.

12. The laboratory device according to claim 8, wherein the processing unit is further configured to provide a correlation between respective locations of each of the M RFID tag(s) and the loading and/or holding and/or processing positions based on the association between the RFID tag(s) with the RFID reader antennae.

13. The laboratory device according to claim 8, wherein the processing unit is further configured to direct communication(s) between the laboratory device and a particular RFID tag through the reader antenna associated with the particular RFID tag, each reader antenna communicating by individually addressing the associated RFID tag.

* * * * *